(12) United States Patent  
Mastri et al.

(10) Patent No.: US 8,317,815 B2
(45) Date of Patent: Nov. 27, 2012

(54) VISUALIZATION TROCAR

(75) Inventors: Dominick Mastri, Bridgeport, CT (US); Kurt Azarbarzin, Fairfield, CT (US)

(73) Assignee: SurgiQuest, Inc., Milford, CT (US)

( * ) Notice: Subject to any disclaimer, the term of this patent is extended or adjusted under 35 U.S.C. 154(b) by 311 days.

(21) Appl. No.: 11/973,123

(22) Filed: Oct. 5, 2007

(65) Prior Publication Data

US 2008/0086160 A1    Apr. 10, 2008

Related U.S. Application Data

(60) Provisional application No. 60/850,006, filed on Oct. 6, 2006, provisional application No. 60/923,921, filed on Apr. 17, 2007.

(51) Int. Cl.
*A61B 17/00* (2006.01)

(52) U.S. Cl. .......................... 606/190; 606/185

(58) Field of Classification Search ............ 606/185, 606/190; 604/264, 272, 273, 274, 284; 600/184
See application file for complete search history.

(56) References Cited

U.S. PATENT DOCUMENTS

| | | | |
|---|---|---|---|
| 3,224,320 A | 12/1965 | Knudsen | |
| 3,357,433 A | 12/1967 | Fourestier et al. | |
| 3,459,189 A | 8/1969 | Alley et al. | |
| 3,556,085 A | 1/1971 | Takahashi | |
| 4,191,191 A | 3/1980 | Auburn | |
| 4,319,563 A | 3/1982 | Kubota | |
| 5,057,082 A | 10/1991 | Burchette, Jr. | |
| 5,058,603 A | 10/1991 | Doi et al. | |
| 5,066,288 A * | 11/1991 | Deniega et al. | 604/274 |
| 5,122,122 A | 6/1992 | Allgood | |
| 5,147,376 A | 9/1992 | Pianetti | |
| 5,159,920 A | 11/1992 | Condon et al. | |
| 5,256,149 A | 10/1993 | Banik et al. | |
| 5,271,380 A | 12/1993 | Riek et al. | |
| 5,290,276 A | 3/1994 | Sewell, Jr. | |
| 5,330,437 A | 7/1994 | Durman | |
| 5,334,150 A * | 8/1994 | Kaali | 604/164.08 |
| 5,342,383 A * | 8/1994 | Thomas | 606/19 |
| 5,376,076 A | 12/1994 | Kaali | |

(Continued)

FOREIGN PATENT DOCUMENTS

DE    25 38 758    3/1977

(Continued)

OTHER PUBLICATIONS

International Preliminary Report on Patentability for PCT/US2007/021387 dated Apr. 7, 2009 together with the Written Opinion of the International Searching Authority (ISA) (10 pages).

(Continued)

*Primary Examiner* — Ryan Severson
*Assistant Examiner* — David Eastwood
(74) *Attorney, Agent, or Firm* — Edwards Wildman Palmer LLP; Scott D. Wofsy; Christopher J. Capelli

(57) ABSTRACT

A surgical trocar and penetrating tip therefor are provided. The tip includes a generally transparent body having proximal and distal ends and an opaque distal tip portion, an integral penetrating edge arranged at a distal end of the body, and inwardly tapered opposed facets formed on the body, converging with one another at the integral penetrating edge.

24 Claims, 18 Drawing Sheets

U.S. PATENT DOCUMENTS

| | | | |
|---|---|---|---|
| 5,380,291 A | 1/1995 | Kaali | |
| 5,385,572 A | 1/1995 | Nobles et al. | |
| 5,391,153 A | 2/1995 | Haber et al. | |
| 5,405,328 A | 4/1995 | Vidal et al. | |
| 5,431,151 A | 7/1995 | Riek et al. | |
| 5,441,041 A | 8/1995 | Sauer et al. | |
| 5,445,142 A | 8/1995 | Hassler, Jr. | |
| 5,467,762 A | 11/1995 | Sauer et al. | |
| 5,545,150 A | 8/1996 | Danks et al. | |
| 5,551,947 A | 9/1996 | Kaali | |
| 5,562,696 A | 10/1996 | Nobles et al. | |
| 5,569,160 A | 10/1996 | Sauer et al. | |
| 5,569,291 A | 10/1996 | Privitera et al. | |
| 5,569,292 A * | 10/1996 | Scwemberger et al. | 606/185 |
| 5,591,192 A | 1/1997 | Privitera et al. | |
| 5,607,440 A | 3/1997 | Danks et al. | |
| 5,607,441 A | 3/1997 | Sierocuk et al. | |
| 5,609,562 A | 3/1997 | Kaali | |
| 5,624,459 A | 4/1997 | Kortenbach et al. | |
| 5,647,840 A | 7/1997 | D'Amelio et al. | |
| 5,658,236 A | 8/1997 | Sauer et al. | |
| 5,674,184 A | 10/1997 | Hassler, Jr. | |
| 5,685,820 A * | 11/1997 | Riek et al. | 600/114 |
| 5,690,664 A | 11/1997 | Sauer et al. | |
| 5,697,913 A | 12/1997 | Sierocuk et al. | |
| 5,707,382 A | 1/1998 | Sierocuk et al. | |
| 5,720,761 A | 2/1998 | Kaali | |
| 5,738,628 A | 4/1998 | Sierocuk et al. | |
| 5,779,728 A | 7/1998 | Lunsford et al. | |
| 5,797,943 A | 8/1998 | Danks et al. | |
| 5,797,944 A * | 8/1998 | Nobles et al. | 606/185 |
| 5,800,451 A | 9/1998 | Buess et al. | |
| 5,817,061 A * | 10/1998 | Goodwin et al. | 604/164.03 |
| 5,817,062 A | 10/1998 | Flom et al. | |
| 5,860,996 A | 1/1999 | Urban et al. | |
| 5,951,464 A | 9/1999 | Takahashi et al. | |
| 5,976,168 A | 11/1999 | Chin | |
| 5,989,228 A | 11/1999 | Danks et al. | |
| 6,007,481 A | 12/1999 | Riek et al. | |
| 6,017,356 A | 1/2000 | Frederick et al. | |
| 6,063,099 A | 5/2000 | Danks et al. | |
| 6,203,568 B1 * | 3/2001 | Lombardi et al. | 623/1.13 |
| 6,206,823 B1 | 3/2001 | Kolata et al. | |
| D443,360 S | 6/2001 | Haberland | |
| 6,277,137 B1 | 8/2001 | Chin | |
| 6,283,948 B1 | 9/2001 | McKernan et al. | |
| 6,439,541 B1 | 8/2002 | Nösel et al. | |
| 6,471,638 B1 | 10/2002 | Chang et al. | |
| 6,478,806 B2 | 11/2002 | McFarlane | |
| 6,613,063 B1 | 9/2003 | Hunsberger | |
| 6,685,630 B2 | 2/2004 | Sauer et al. | |
| 6,692,467 B2 | 2/2004 | McFarlane | |
| 6,830,578 B2 | 12/2004 | O'Heeron et al. | |
| 6,835,201 B2 * | 12/2004 | O'Heeron et al. | 606/184 |
| 6,863,674 B2 | 3/2005 | Kasahara et al. | |
| 6,884,253 B1 | 4/2005 | McFarlane | |
| 6,908,454 B2 | 6/2005 | McFarlane | |
| 6,918,871 B2 | 7/2005 | Schulze | |
| 6,939,296 B2 | 9/2005 | Ewers et al. | |
| 6,960,164 B2 | 11/2005 | O'Heeron | |
| 2002/0013597 A1 | 1/2002 | McFarlane | |
| 2002/0143236 A1 | 10/2002 | Sauer et al. | |
| 2004/0158126 A1 * | 8/2004 | Sauer et al. | 600/114 |
| 2005/0075605 A1 | 4/2005 | Lyon | |
| 2005/0107815 A1 * | 5/2005 | McFarlane | 606/185 |
| 2005/0107816 A1 * | 5/2005 | Pingleton et al. | 606/185 |
| 2005/0251190 A1 | 11/2005 | McFarlane | |
| 2005/0261717 A1 | 11/2005 | Sauer et al. | |
| 2008/0086160 A1 | 4/2008 | Mastri et al. | |

FOREIGN PATENT DOCUMENTS

| | | |
|---|---|---|
| DE | 2847561 A1 | 5/1980 |
| DE | 41 33 073 A1 | 4/1992 |
| EP | 0 484 725 B1 | 5/1992 |
| EP | 0 577 400 B1 | 1/1994 |
| EP | 0577 400 A1 | 1/1994 |
| EP | 0 664 992 A1 | 8/1995 |
| EP | 0 664 992 B1 | 8/1995 |
| EP | 1685792 A1 | 8/2006 |
| EP | 1 707 132 A2 | 10/2006 |
| EP | 1 707 132 B1 | 10/2006 |
| GB | 2173312 A | 10/1986 |
| WO | WO 94/11040 | 5/1994 |

OTHER PUBLICATIONS

International Search Report and Written Opinion dated May 24, 2011 for international application PCT/US2011/032305.
Office Action dated Nov. 10, 2011 for European Patent Application No. 07 839 288.3.
International Search Report dated Jul. 30, 2008.

* cited by examiner

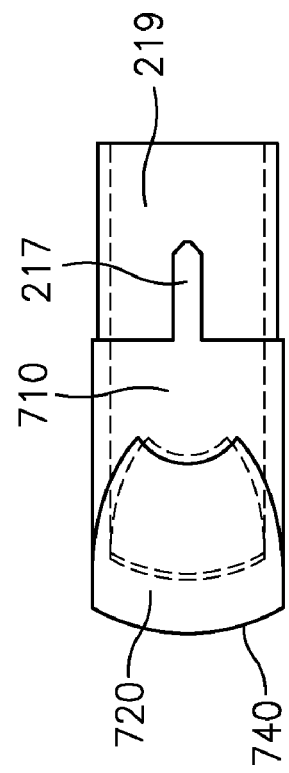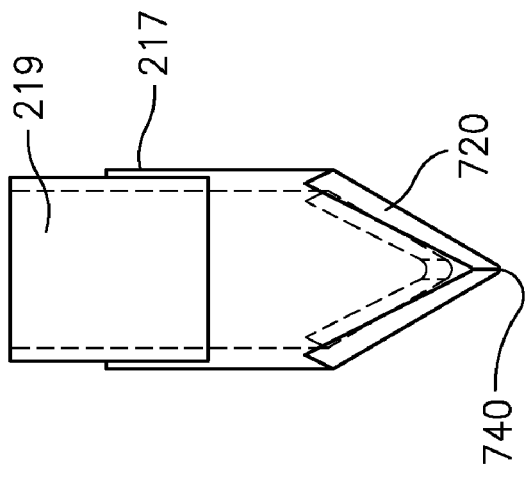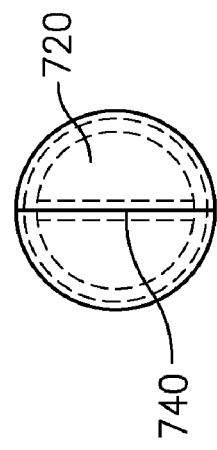

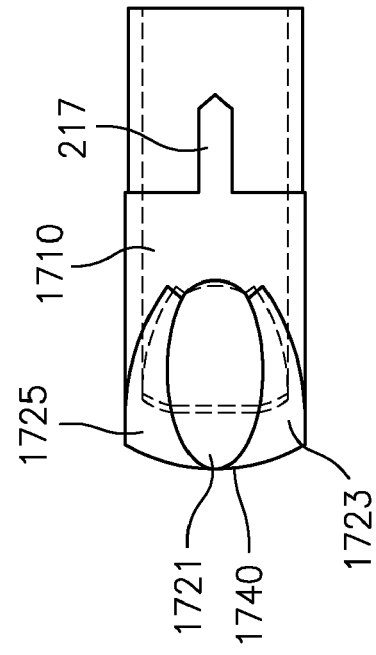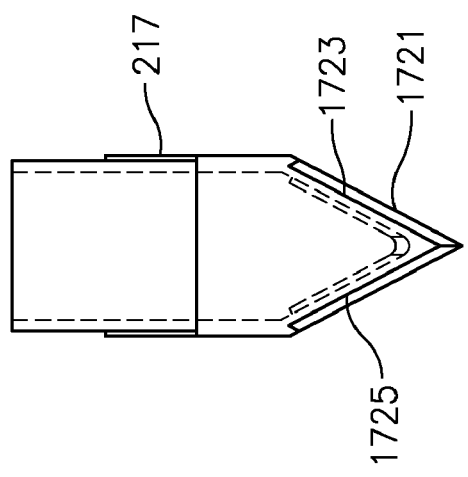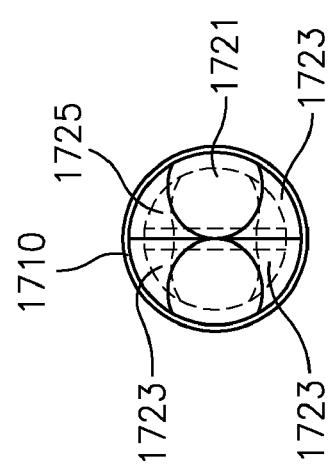

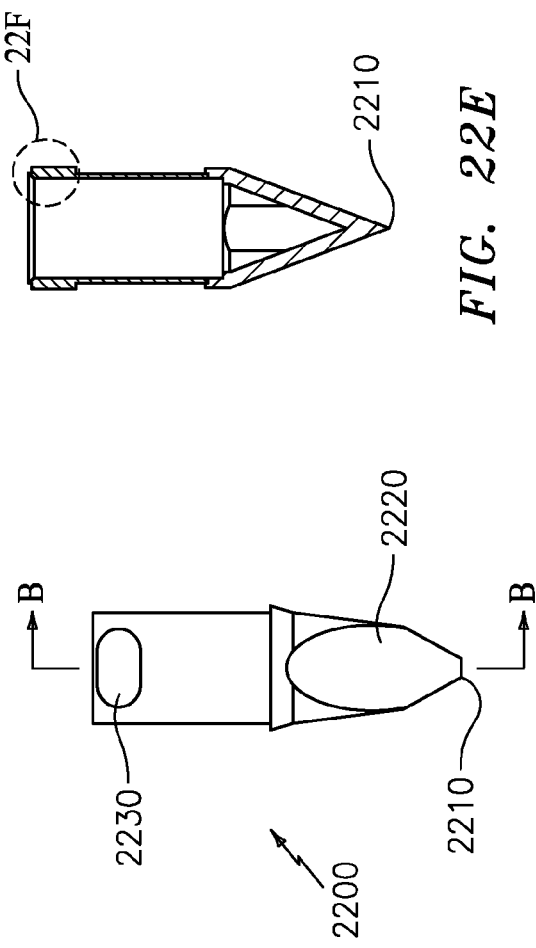
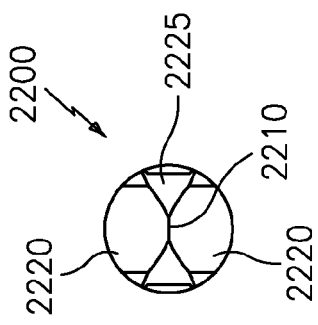
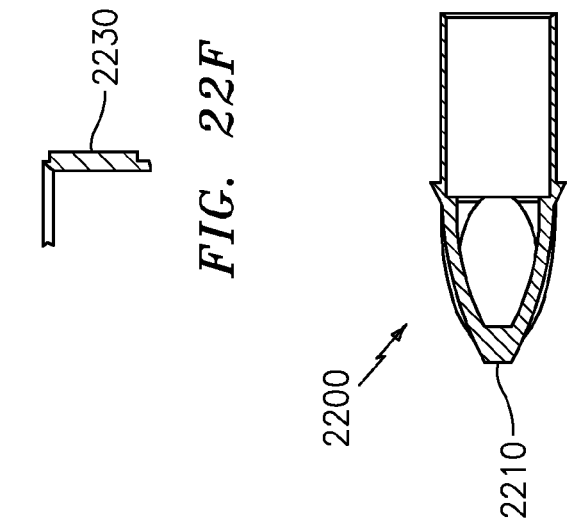
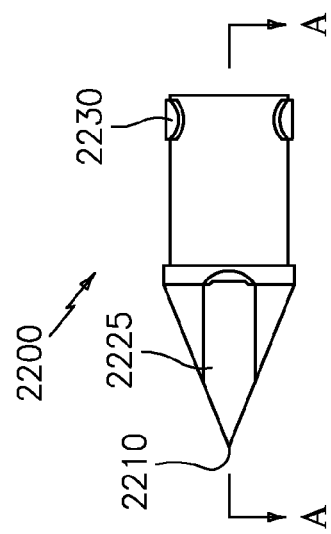
FIG. 22F
FIG. 22D
FIG. 22C
FIG. 22E
FIG. 22A
FIG. 22B

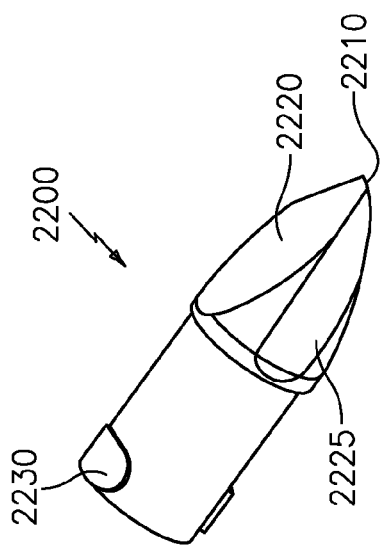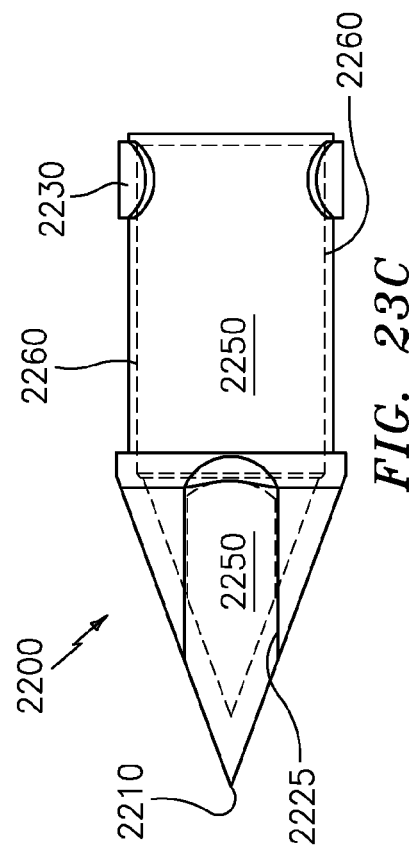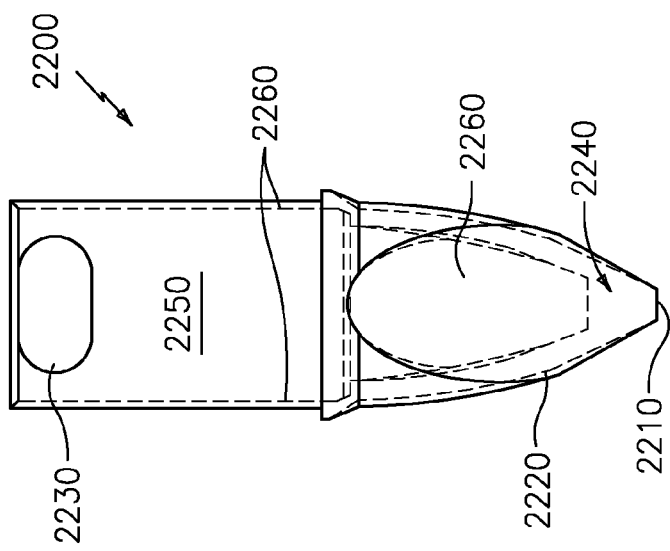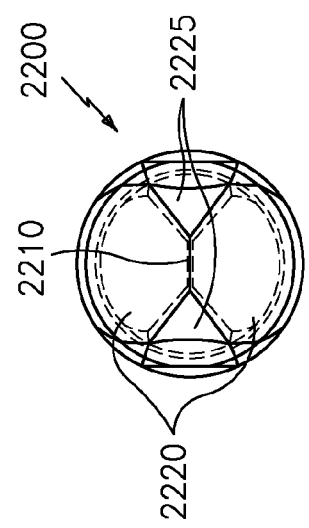

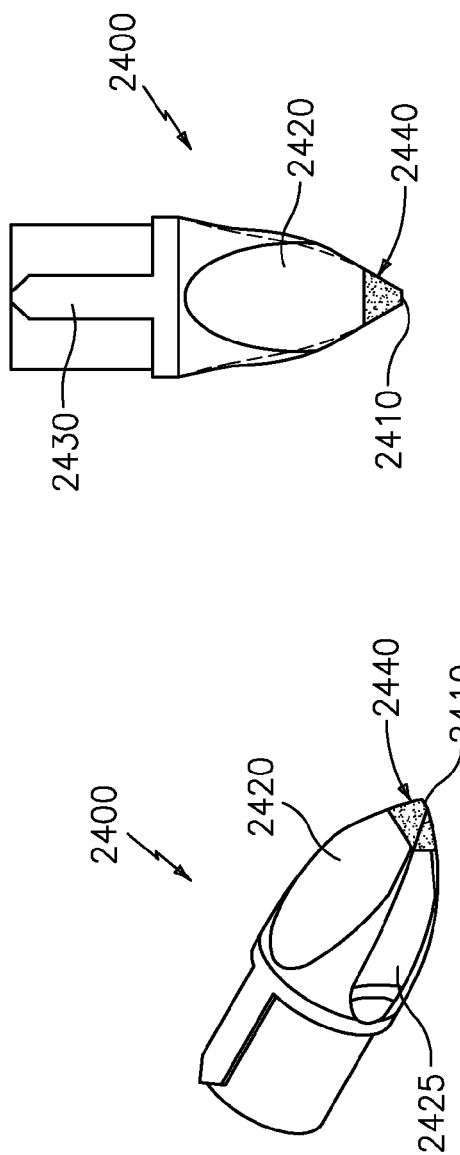
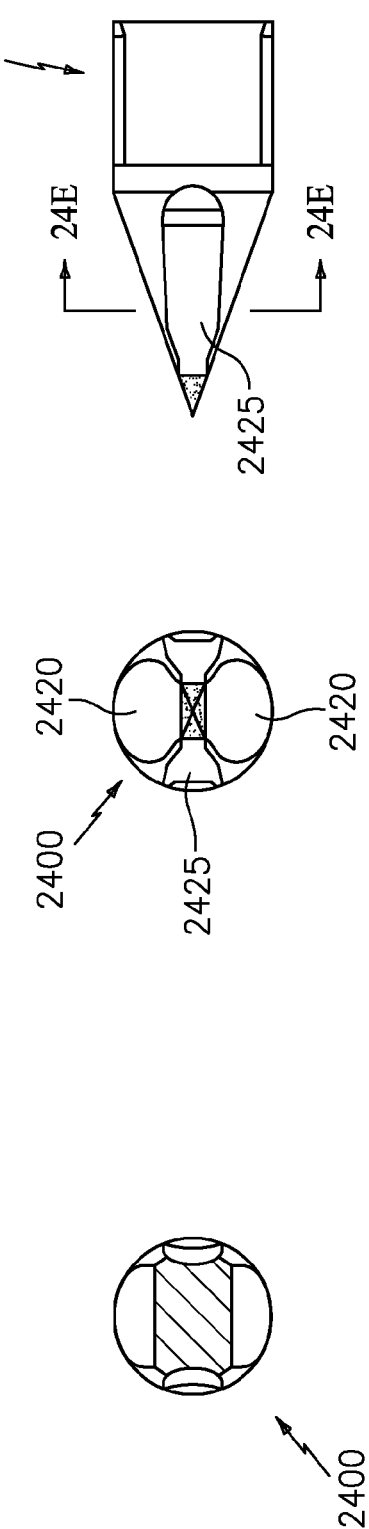
FIG. 24A
FIG. 24B
FIG. 24C
FIG. 24D
FIG. 24E

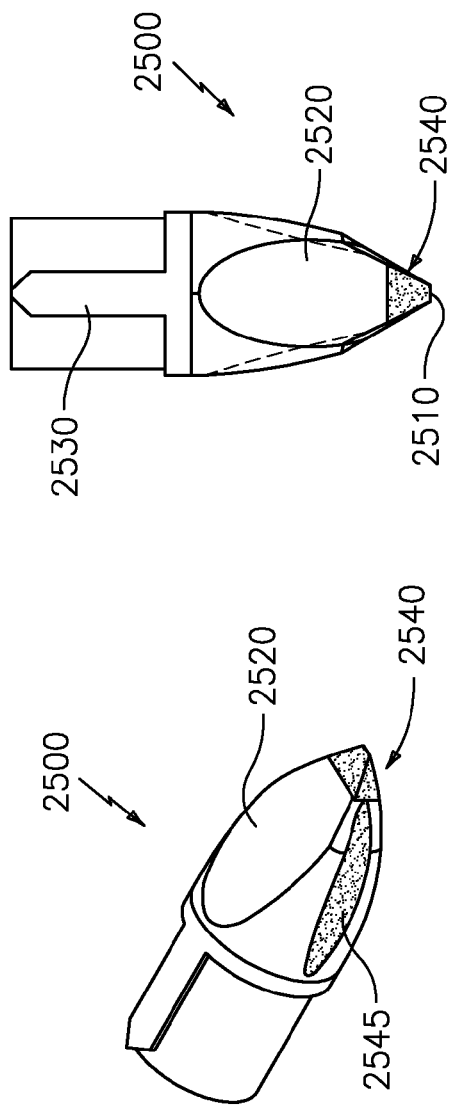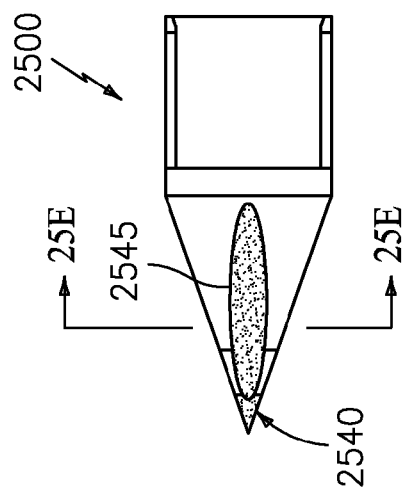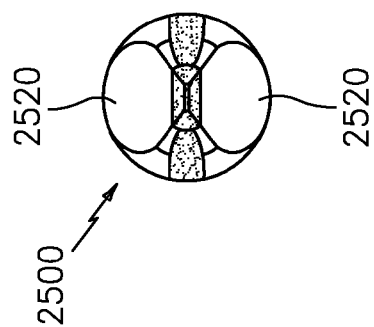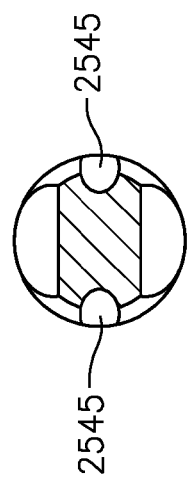
FIG. 25A
FIG. 25B
FIG. 25C
FIG. 25D
FIG. 25E

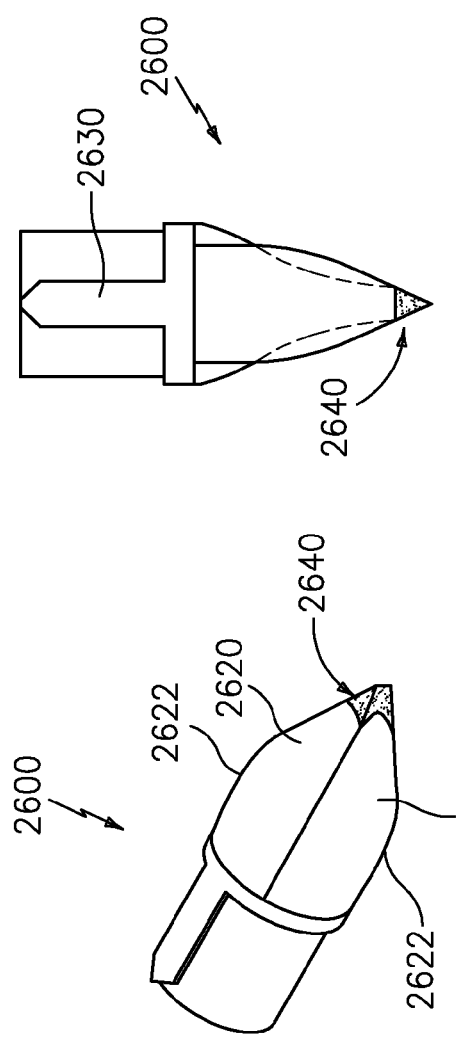
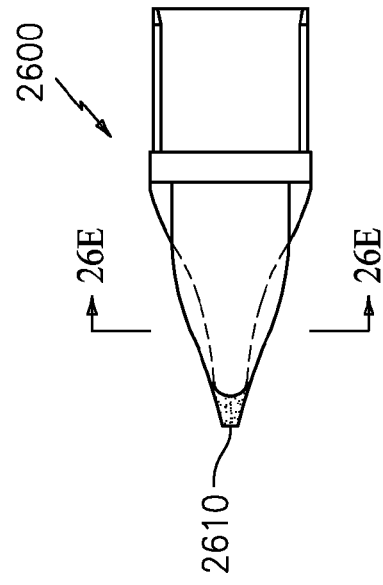
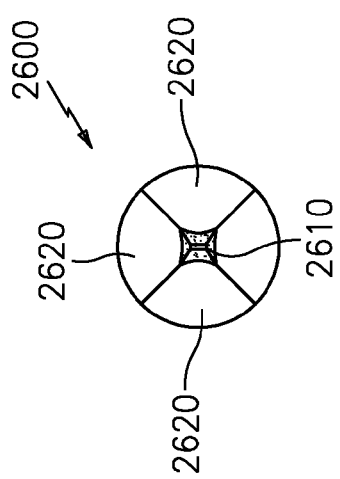
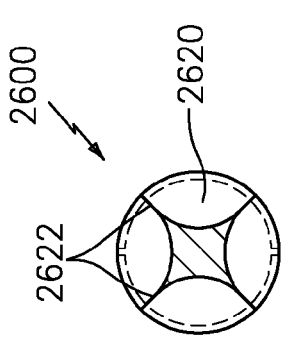
FIG. 26A
FIG. 26B
FIG. 26C
FIG. 26D
FIG. 26E

VISUALIZATION TROCAR

CROSS-REFERENCE TO RELATED APPLICATIONS

This application claims priority to U.S. Provisional Application No. 60/923,921 filed Apr. 17, 2007 and to U.S. Provisional Application No. 60/850,006 filed Oct. 6, 2006. Each of the foregoing provisional applications is incorporated herein by reference in its entirety.

BACKGROUND OF THE INVENTION

1. Field of the Invention

The present invention relates to surgical instruments such as trocars for use in insertion of surgical access devices, such as access cannulas. Particularly, the present invention is directed to such insertion devices having a transparent tip to allow visualization of tissue being penetrated.

2. Description of Related Art

A variety of devices and methods are known in the art for insertion of surgical access devices, such as surgical cannulas in minimally-invasive surgical procedures. Of such devices, many are configured to puncture a patient's abdominal wall. Most of such insertion devices are fully solid and opaque, so a surgeon cannot easily visually differentiate between layers of the abdominal wall and internal abdominal organs.

Some insertion devices have been developed that include a transparent tip or an integral endoscope While such devices can offer improved guidance to a surgeon over those with no means for visualization, such devices can be relatively complex, difficult to manufacture, and therefore can be expensive. Accordingly, there still remains a need in the art for an insertion device that is capable of visually guiding puncture of an abdominal wall and, optionally, concurrent insertion of a surgical access device. There further remains a need for such a device that is relatively inexpensive and easy to fabricate. The present invention provides a solution for these foregoing problems.

SUMMARY OF THE INVENTION

The purpose and advantages of the present invention will be set forth in and apparent from the description that follows. Additional advantages of the invention will be realized and attained by the methods and systems particularly pointed out in the written description and claims hereof, as well as from the appended drawings.

To achieve these and other advantages and in accordance with the purpose of the invention, as embodied, includes a penetrating tip for a surgical trocar. The penetrating tip includes a generally transparent body, having proximal and distal ends. The body has an opaque distal tip portion, which can be used as a guide or indicator, and/or to reduce glare, as described in more detail below. The body also has an integral penetrating edge arranged at a distal end of the body, and inwardly tapered opposed facets formed in the body, converging with one another at the integral penetrating edge, which can be a dissecting edge, a cutting edge or a blunt edge, for example. Alternatively, the penetrating edge is arranged on the tip in the distal end portion thereof, and not necessarily at the distal end thereof.

In accordance with the invention, the tip can further include an expanded-diameter region for engaging a surgical access device. The tip can be formed by molding, such as by injection molding. The tip's opposed facets can be convexly curved, substantially planar, or a combination thereof. Opposed facets are provided on the tip at a predetermined angle with respect to one another, such as at 20 degrees or 30 degrees. In other embodiments in accordance with the invention, the facets are provided at an angle of about 40 degrees, with respect to one another. It is therefore to be understood that a relative angle of between about 5 and about 90 degrees, at any increment of one-degree therebetween may be used for tips in accordance with the invention.

In accordance with the invention, the penetrating edge of the tip can be substantially straight or convexly arcuate in configuration. If desired, a locking element can be provided on the body for engaging a trocar or other insertion device. Tips in accordance with the invention can further include an inner optical surface configured so as to minimize distortion of images taken through the penetrating tip. The tips can be formed of a plastic material, which can be, for example, polycarbonate plastic or polymethyl methacrylate.

In accordance with another aspect of the invention, a surgical trocar is provided having a handle, a shaft extending from the handle and a penetrating tip. The penetrating tip includes a generally transparent body having proximal and distal ends. The body has an opaque distal tip portion, an integral penetrating edge arranged at a distal end of the body, and inwardly tapered opposed facets formed in the body, converging with one another at the integral penetrating edge. The trocar can further include an optical path extending from the tip to an imaging device. The imaging device can be, for example, a CCD sensor or an optical eyepiece. Further, the imaging device can be provided in the shaft of the surgical trocar or external thereto. In accordance with a further aspect of the invention, the trocar can further include an access device, configured and dimensioned to receive the shaft of the trocar.

In accordance with still another aspect of the invention, a kit is provided having a package for holding kit contents and storing kit contents in a sterile environment, a surgical trocar and one or more penetrating tips for the surgical trocar. The surgical trocar has a handle, and a shaft extending from the handle. The penetrating tips for the surgical trocar each have a generally transparent body having proximal and distal ends. The body has an opaque distal tip portion, and an integral edge arranged at a distal end of the body and inwardly tapered opposed facets formed in the body, converging with one another at the integral edge.

It is to be understood that both the foregoing general description and the following detailed description are exemplary and are intended to provide further explanation of the invention claimed.

BRIEF DESCRIPTION OF THE DRAWINGS

The accompanying drawings, which are incorporated in and constitute part of this specification, are included to illustrate and provide a further understanding of the invention. Together with the description, the drawings serve to explain the principles of the invention, wherein:

FIG. 9 is a side view of the penetrating tip of FIG. 7, including hidden lines illustrating internal surface geometry;

FIG. 10 is an end view of the penetrating tip of FIG. 7, including hidden lines illustrating internal surface geometry;

FIG. 11 is a top view of the penetrating tip of FIG. 7, including hidden lines illustrating internal surface geometry;

FIG. 19 is a side view of the penetrating tip of FIG. 17, including hidden lines illustrating internal surface geometry;

FIG. 20 is an end view of the penetrating tip of FIG. 17, including hidden lines illustrating internal surface geometry;

FIG. 21 is a top view of the penetrating tip of FIG. 17, including hidden lines illustrating internal surface geometry;

FIGS. 22A-22F are views of a further embodiment of a penetrating tip constructed in accordance with the present invention;

FIGS. 23A-23D are further views of the embodiment of FIG. 22;

FIGS. 24A-24E are views of still another embodiment of a penetrating tip constructed in accordance with the present invention;

FIGS. 25A-25E are views of yet another embodiment of a penetrating tip constructed in accordance with the present invention; and FIGS. 26A-26E are views of another embodiment of a penetrating tip constructed in accordance with the present invention.

DETAILED DESCRIPTION OF THE PREFERRED EMBODIMENT

Reference will now be made in detail to the present preferred embodiments of the invention, examples of which are illustrated in the accompanying drawings.

The present invention may be used for insertion of surgical access devices or other devices that require the puncture of biological tissue. The present invention is particularly suited for insertion of surgical access devices or cannulas (or "cannulae") through the abdominal wall of a patient, in order to provide a working channel through which a surgical procedure can be performed.

Figure 1:
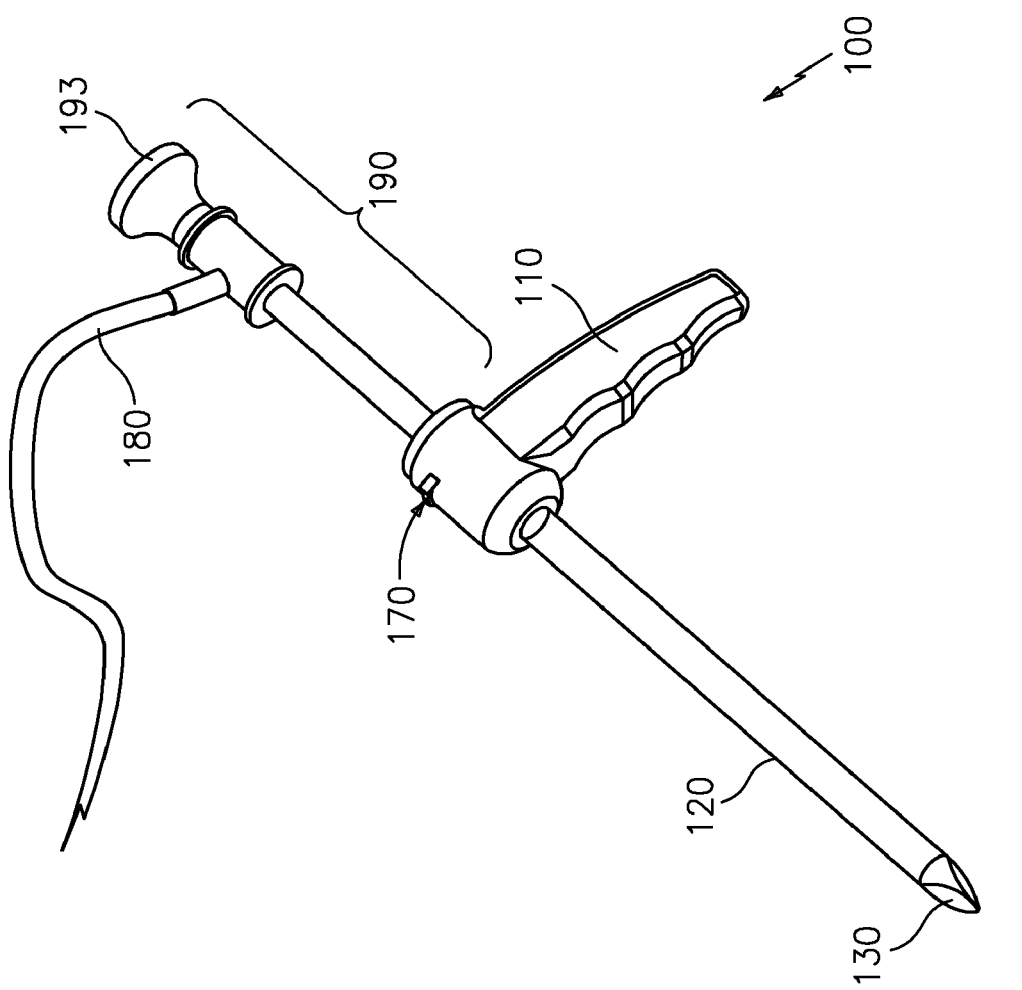
FIG. 1 is an isometric view of an exemplary embodiment of a trocar in accordance with the present invention, for use with penetrating tips constructed in accordance with the invention.

In accordance with the invention, as seen in FIG. 1, a visualization trocar 100 is provided, which includes a handle 110, a shaft 120 extending from the handle 110, and a penetrating tip 130 arranged at the distal end of the shaft 120. As illustrated, the trocar 100 can be used with an endoscope 190 having an eyepiece 193 at a distal end thereof, which receives images through an optical path from a lens (not shown) situated on the endoscope 190 near the penetrating tip 130. Such images are typically transmitted by way of a transparent medium within the endoscope 190, such as an optical shaft or one or more optical fibers. If it is desired that images be displayed on an external monitor, an attachment having an image sensor can be secured to the endoscope 190 on or in place of the eyepiece 193. The endoscope 190 can further be provided with a secondary optical conduit 180, which can transmit light to the penetrating tip 130. Further in accordance with the invention, the trocar 100 can be provided with an integral endoscope, including all of the features thereof contained in one integral device.

Alternatively, if desired, an image sensor can be provided within the trocar 100 at the distal end thereof—in the shaft 120 or within the penetrating tip 130. Accordingly, electrical rather than optical connections then extend through the shaft 120 to a display device, such as a video monitor.

Additionally a locking element 170 can be provided in the handle portion 110 of the trocar 100. The locking element 170, as embodied, engages the endoscope 190 passing through the handle 110, to prevent at a minimum, relative axial movement between the trocar 100 and the endoscope 190. Additionally, relative rotational movement can be inhibited, if desired.

The precise configuration of the trocar 100 itself can vary, and can include additional features, as needed or desired. Moreover, cannulae utilized with the trocar 100, whether rigid or flexible, can include one or more demarcations thereon, which indicate the progress of insertion, and can therefore signal to the surgeon when the cannula has been inserted sufficiently.

Also, the geometry of the penetrating tip 130 can change as desired, as will become apparent through understanding of the various embodiments of penetrating tips, which are set forth hereinbelow. It should be noted that the term "trocar" is used herein to refer generally to an insertion device, which is capable of puncturing an anatomical structure, such as an abdominal wall, to insert a surgical access device or "port" to aid in performing a surgical procedure.

Figure 2:
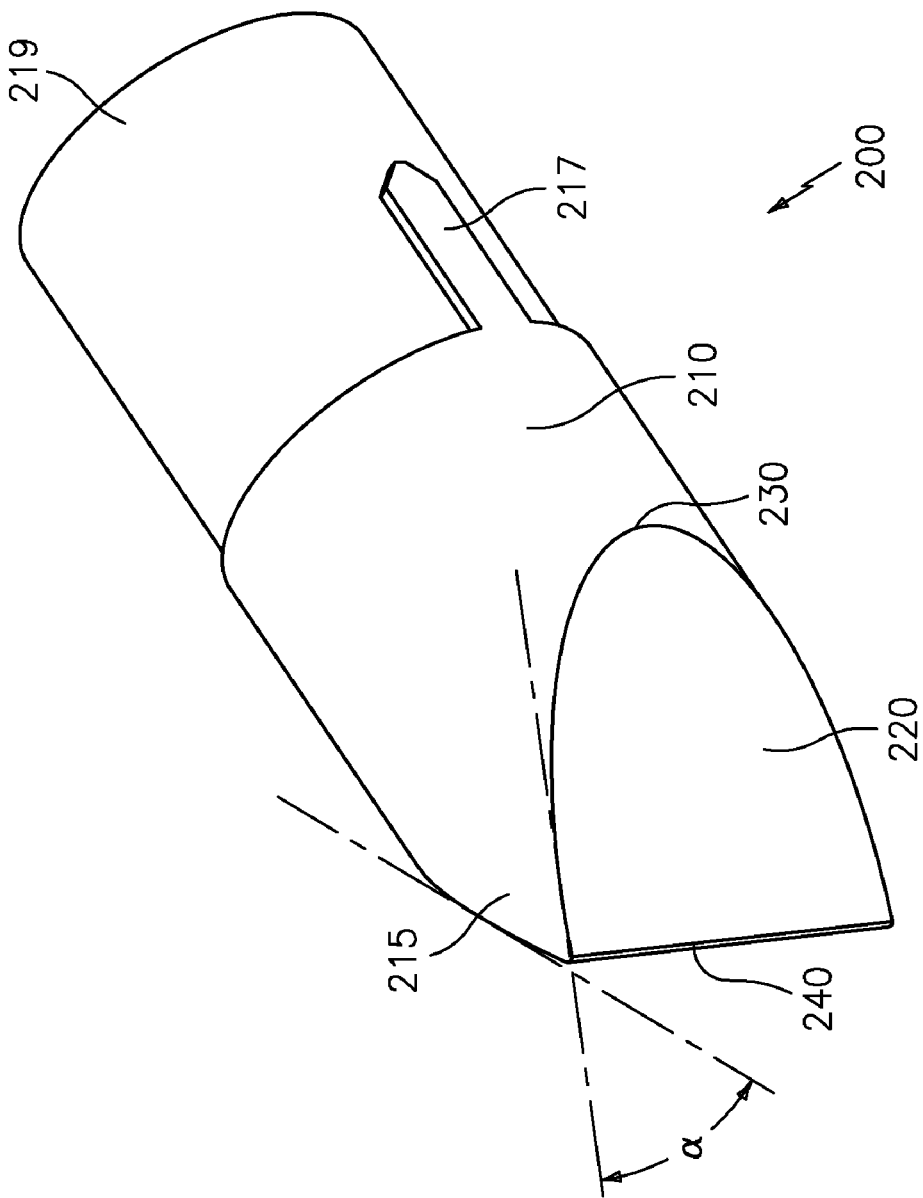
FIG. 2 is an isometric view of one embodiment of a penetrating tip in accordance with the invention, which includes a substantially straight edge.

For the purposes of explanation and illustration, and not limitation, an isometric view of an exemplary embodiment of a penetrating tip in accordance with the invention is shown in FIG. 2 and is designated generally by reference number 200. The penetrating tip 200 includes a body 210, at its proximal end having a reduced-diameter portion 219, and one or more rotation locking elements 217, each of which interfaces with the shaft of a trocar (e.g., shaft 120 of trocar 100). The reduced-diameter portion 219 is inserted into the shaft of a trocar, thereby enabling secure mutual engagement therebetween, while the rotation locking element(s) 217 engage a mating element, such as a groove, notch or recess in the shaft of the trocar, preventing relative rotation between the penetrating tip 200 and the trocar shaft. If, however, the tip 200 is manufactured integrally with a trocar, relative positioning can be achieved and maintained in another manner, such as integrally molding, insert molding, adhering, bonding or welding the components by heat, solvent or friction, or by another suitable manufacturing technique.

The distal end of the penetrating tip 200 includes a distal taper 215 of the body 210, and two opposed angled facets 220, which are angled inwardly, approaching the penetrating edge 240 at the distal end of the tip 200. The facets 220 are substantially planar in this embodiment, and are delimited partially by a change in contour indicated by arcuate contour interface 230 with the body 210, and partially by the distal penetrating edge 240. The facets 220 are angled, with respect to one another at an angle α (alpha). The angle α can be anywhere from about 5 degrees to about 90 degrees, inclusive, at any one-degree increment therebetween. In one embodiment, the angle α is about 30 degrees, and in another embodiment the angle α is about 40 degrees, for example.

In use, the tip 200 is inserted into a trocar, such as trocar 100 of FIG. 1, or alternatively is manufactured integrally therewith. The tip 200 can be manufactured from any suitable material, but is preferably transparent, to allow a surgeon to view the layers of tissue through which the surgeon is penetrating. Such materials can include, for example, polycarbonate plastic, polymethyl methacrylate ("acrylic"), a vitreous material such as glass, or an optical crystal material. Accordingly, the surgeon is able to view the tissue through which the trocar and tip 200 are passing. The surgeon is able, therefore, to determine by the general appearance of the tissue, the point at which the tip 200 has penetrated to a sufficient depth. During an abdominal procedure, the depth will typically be a point at which the tip 200 has just entered the peritoneal cavity.

Further, in accordance with the invention, the tip 200 can be provided with any desired degree of sharpness. That is, the penetrating tip 240 can be formed to have a sharp point, a dissecting edge or can be rounded to any desired degree in order to provide a relatively blunt leading edge. When provided with a relatively blunt tip 240, accidental injury to internal anatomical structures, such as intestines, can be reduced.

Figure 3:
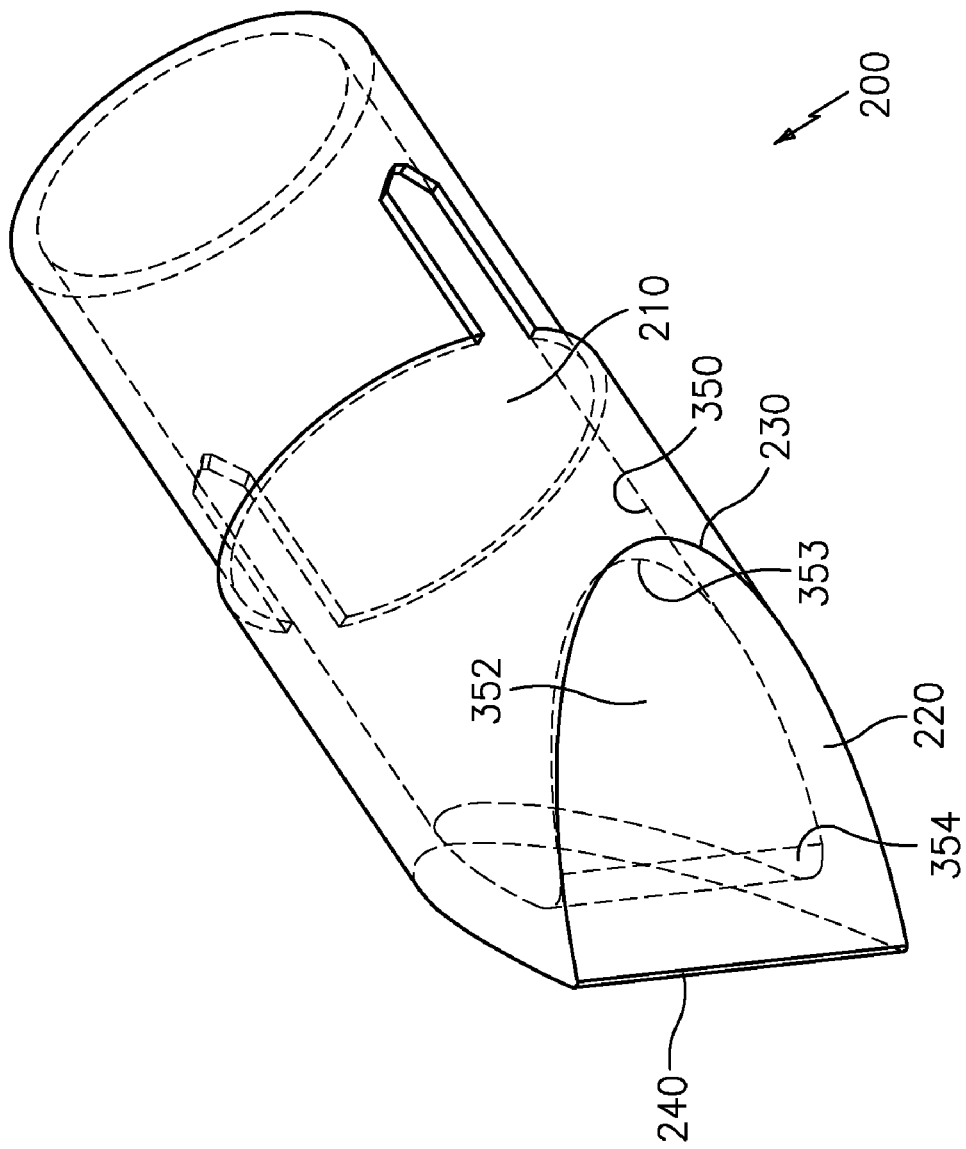
FIG. 3 is an isometric view of the penetrating tip of FIG. 2, including hidden lines illustrating internal surface geometry of the tip.

FIG. 3 is an isometric view of the tip of FIG. 2, including hidden lines illustrating internal surface geometry of the tip 200. As can be seen, an internal surface 350 is provided in the penetrating tip 200. This internal surface 350 defines a space through which images can be taken. A visualization device (not shown) is preferably provided with trocars and penetrating tips in accordance with the invention, including that illustrated in FIGS. 2-6. Various embodiments can be used to provide an image to the surgeon inserting the trocar. For example, an imaging device such as a CCD (charge-coupled device) can be provided in the trocar (e.g., trocar 100) or in the penetrating tip (e.g., tip 200), or alternatively connected thereto via an optical path, which can include, for example, one or more fiber-optic conduits. Such trocars can also be provided with illumination capability provided through the optical path.

The internal space defined by the internal surface 350 of the tip 200 includes surface features that correspond to features provided on the external surface of the tip 200. As can be seen, an arcuate contour interface 353 and inner facet 352 correspond to the arcuate contour interface 230 and the facets 220 of the outer surface of the tip 200. Moreover, an inner tip 354 of the space defined by the inner surface 350 corresponds to the penetrating edge 240 of the outer surface of the tip 200. Such corresponding internal geometry can reduce distortion in an image obtained from the tip 200. If desired, one or more lenses can be additionally provided within the tip 200, to adjust, correct or direct images as needed.

Figure 6:
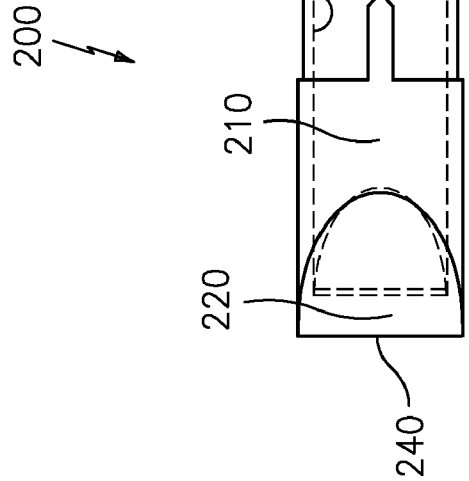
FIG. 6 is a top view of the penetrating tip of FIG. 2, including hidden lines illustrating internal surface geometry.
Figure 4:
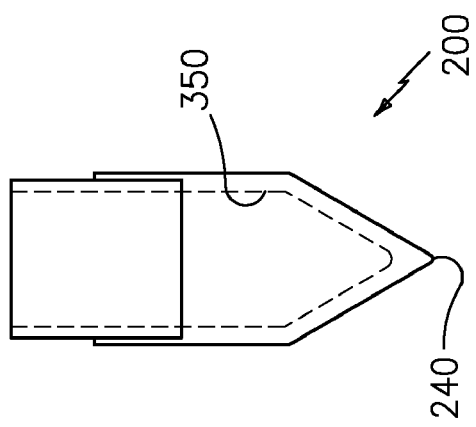
FIG. 4 is a side view of the penetrating tip of FIG. 2, including hidden lines illustrating internal surface geometry.
Figure 5:
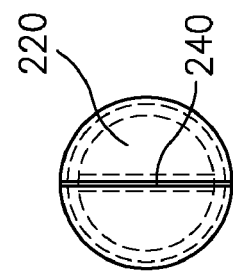
FIG. 5 is an end view of the penetrating tip of FIG. 2, including hidden lines illustrating internal surface geometry.

FIGS. 4, 5 and 6 are side, end and top views, respectively, of the tip 200 of FIGS. 2 and 3, including hidden lines illustrating internal surface geometry of the tip 200. Naturally, any of the features described in connection with any of the following embodiments can advantageously be applied to this embodiment.

FIGS. 7-11 illustrate an alternate embodiment of a penetrating tip 700 in accordance with the invention, having an arcuate penetrating surface 740. As with the embodiment of FIGS. 2-6, the tip 700 includes a body 710, having at its proximal end a reduced-diameter portion 219, and one or more rotation locking elements 217. Naturally, if the tip 700 is manufactured integrally with a trocar, relative positioning can be achieved and maintained without such locking elements 217.

The distal end of the penetrating tip 700 includes a distal taper 715 of the body 710, and two opposed angled facets 720, which are angled inwardly, approaching the cutting or dissecting edge 740 at the distal end of the tip 700. Again, the facets 720 are delimited partially by an arcuate contour interface 730 with the body 210, and partially by the distal edge 740. In this embodiment, the facets 720 are convexly contoured, rather than being planar, which can best be seen in the side view of FIG. 9. The facets 720 are angled, with respect to one another at an angle α (alpha). The angle α can be, for example, anywhere from about 5 degrees to about 80 degrees.

Figure 7:
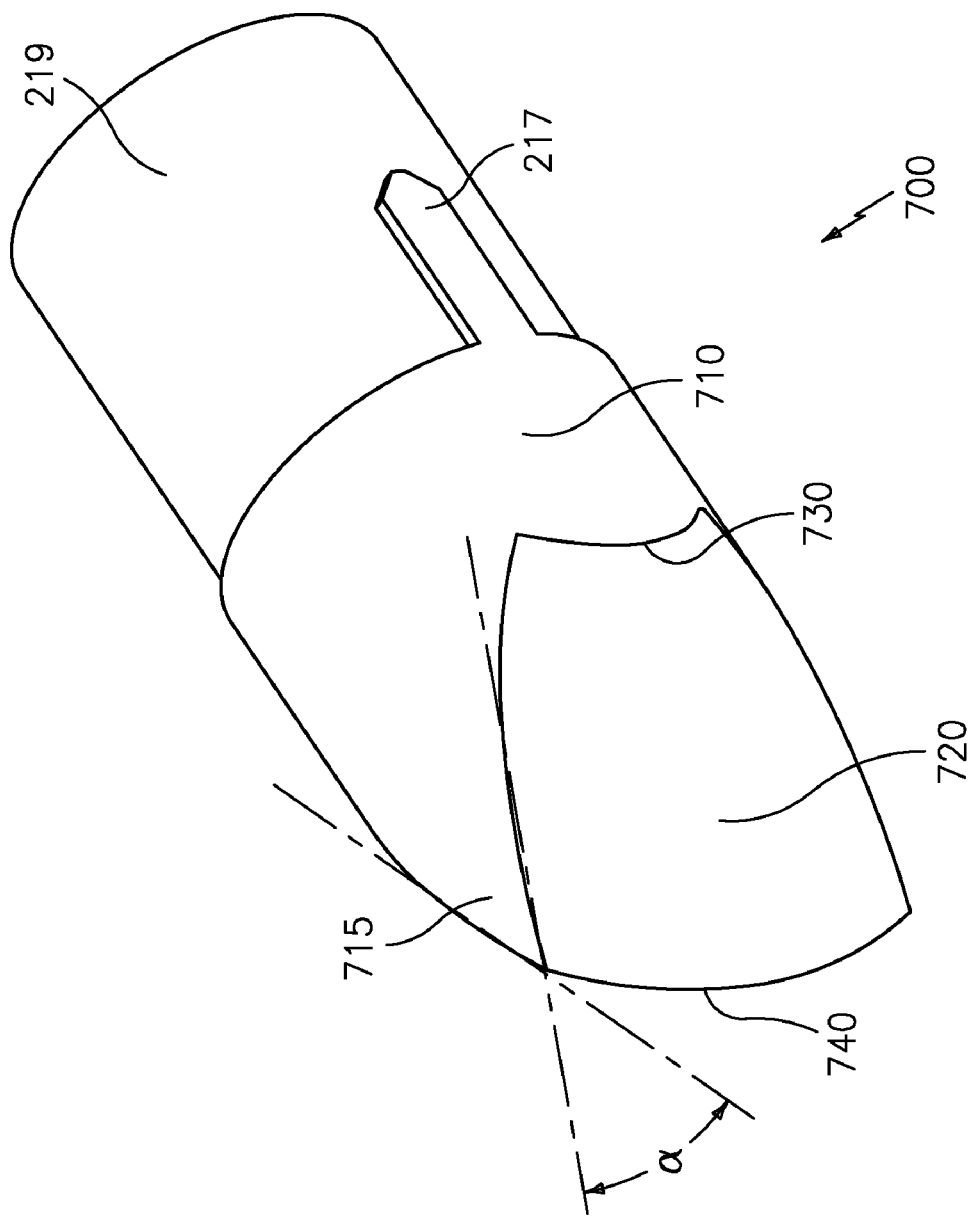
FIG. 7 is an alternate embodiment of a penetrating tip in accordance with the invention, having an arcuate penetrating surface.
Figure 8:
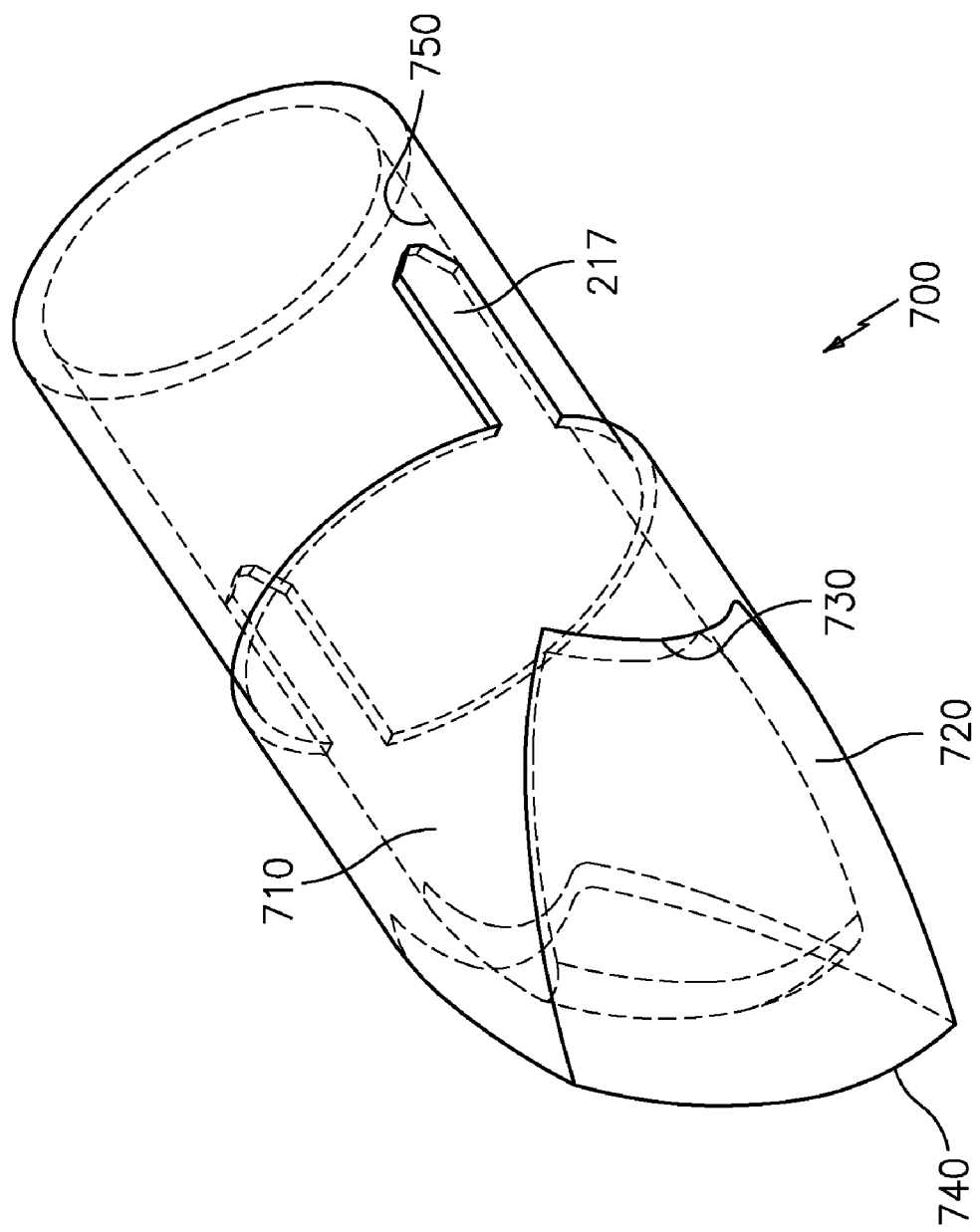
FIG. 8 is an isometric view of the penetrating tip of FIG. 7, including hidden lines illustrating internal surface geometry of the tip.

FIG. 8 is an isometric view of the tip 700 of FIG. 7, including hidden lines illustrating internal surface geometry of the tip 700. As with the foregoing embodiment of FIGS. 2-6, an internal surface 750 is formed within the tip 700, which includes surface features corresponding to features of the outer surface of the tip 700. Alternatively, any of the embodiments set forth herein can include a solid tip. Preferably, however, such tip will include optical elements to enable adequate optical transmission of images from the distal end of the tip 700. Alternatively still, if an imaging device, such as a CCD is provided within the body 710 of the tip 700 at an appropriate location, such as just proximal of the facet 720, an adequate image can be obtained regardless of the optical characteristics of the remainder of the tip 700.

FIGS. 9-11 are side, end and top views of the tip 700 of FIGS. 7-8, including hidden lines illustrating internal surface geometry. Naturally, any of the features described in connection with any other embodiment set forth herein can advantageously be applied to this embodiment.

FIGS. 12-16 illustrate a further embodiment of a penetrating tip, designated generally with reference number 1200, in accordance with the invention. The tip 1200 includes ovoid facets 1120 formed thereon, terminating in an arcuate cutting or dissecting surface 1240. The tip 1200 is similar in many respects to the foregoing embodiments. However, the ovoid facets 1220 result in a reduced profile for insertion. That is, instead of the relatively wide surfaces 240, 740 of the above-described tips 200, 700, respectively, the cutting or dissecting edge 1240, at the distal end of the ovoid facets 1220, is relatively narrow. This aspect of the tip 1200, can facilitate initial insertion by reducing the force necessary to puncture the abdominal wall. The tapered region 1215 of the body 1210, helps widen the initial incision, as the tip 1200 advances through the patient's abdominal wall. The ovoid facets 1220 can be convex or planar, as desired, and are delimited by the penetrating edge 1240, and the contour interface 1230, where the contour of the tip 1200 transitions from the facet 1220 to the relatively cylindrical body 1210. Moreover, the facets 1220 are angled with respect to one another at an angle α (alpha). The angle α can be anywhere from about 5 degrees to about 80 degrees, for example.

Figure 12:
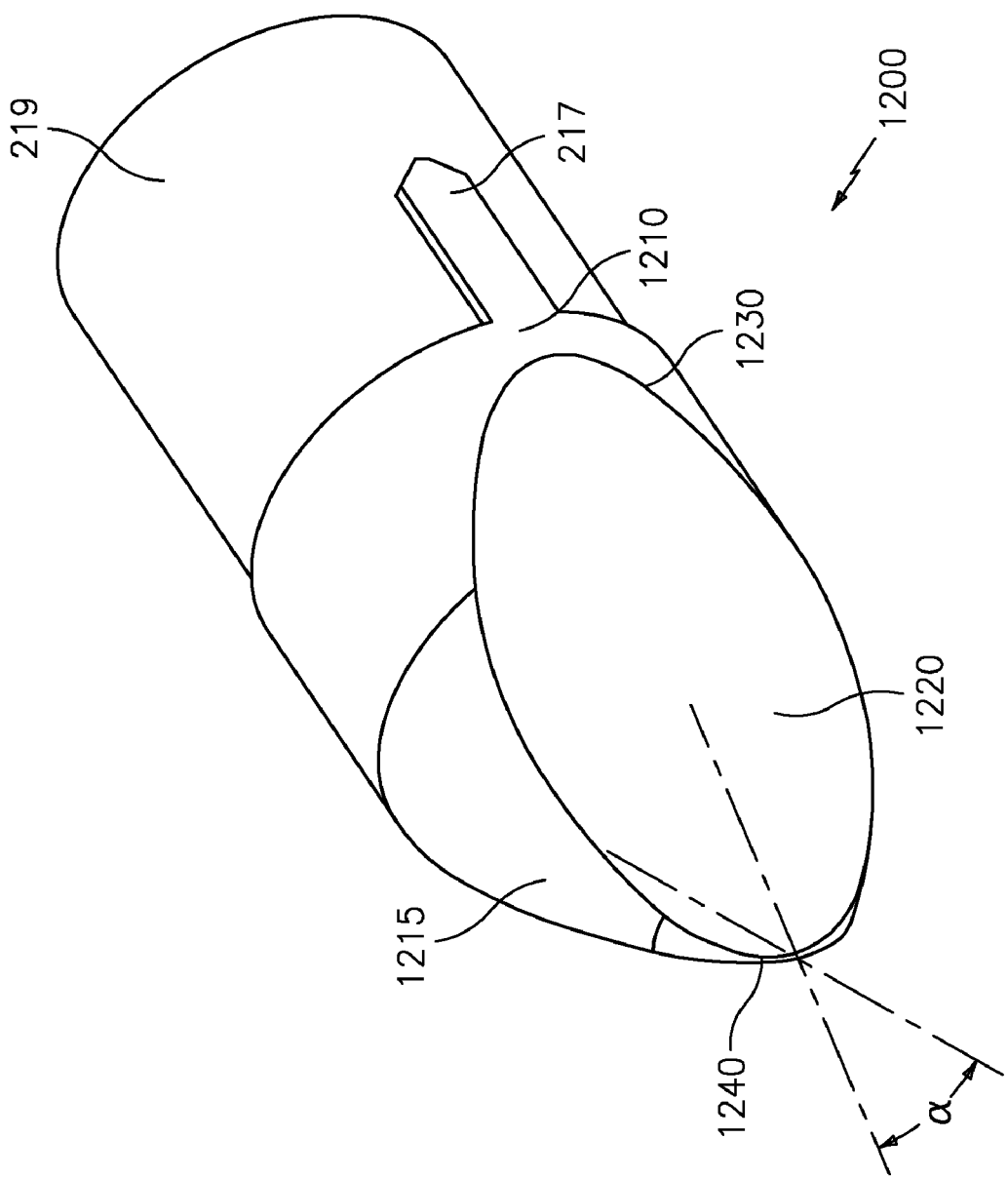
FIG. 12 is a further embodiment of a penetrating tip in accordance with the invention having ovoid facets formed thereon, terminating in an arcuate penetrating edge.
Figure 13:
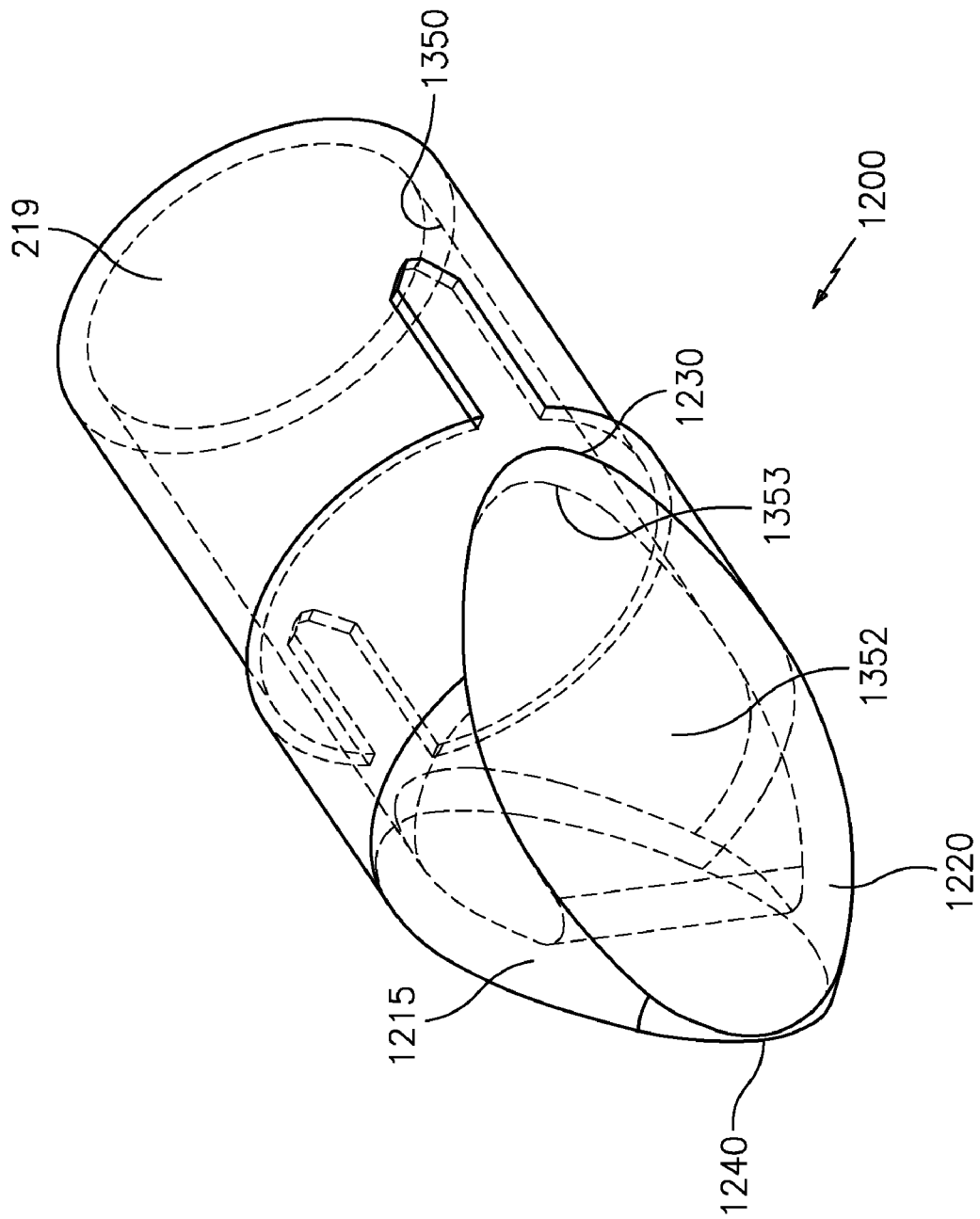
FIG. 13 is an isometric view of the penetrating tip of FIG. 12, including hidden lines illustrating internal surface geometry of the tip.

FIG. 13 is an isometric view of the tip 1200 of FIG. 12, including hidden lines illustrating internal surface geometry of the tip 1200. In this view, the internal surface 1350 of the tip 1200 is visible. As with foregoing embodiments, the internal surface 1350 can include features that correspond to features of the outer surface of the tip 1200. For example, the tip 1200 can include a contour interface 1353 corresponding to the contour interface 1230 of the outer surface of the tip 1200, and can include an inner facet 1352 corresponding to the facet 1220 on the outer surface of the tip 1200.

Figure 16:
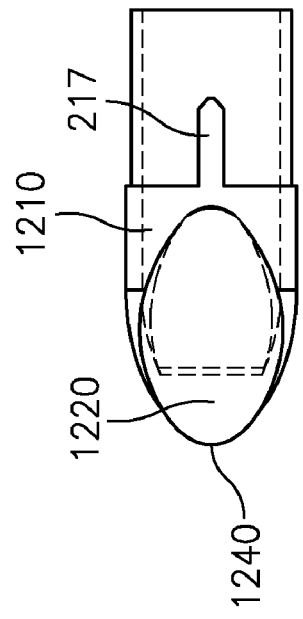
FIG. 16 is a top view of the penetrating tip of FIG. 12, including hidden lines illustrating internal surface geometry.
Figure 14:
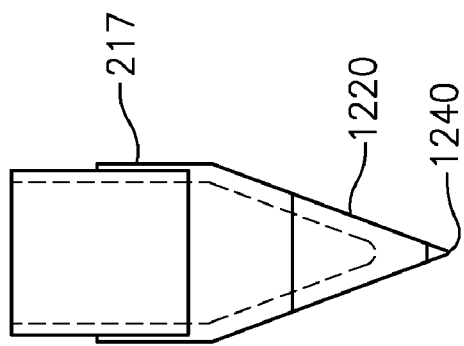
FIG. 14 is a side view of the penetrating tip of FIG. 12, including hidden lines illustrating internal surface geometry.
Figure 15:
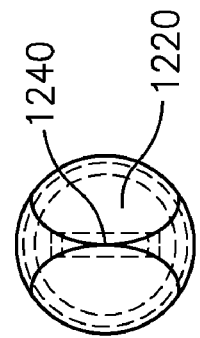
FIG. 15 is an end view of the penetrating tip of FIG. 12, including hidden lines illustrating internal surface geometry.

FIGS. 14-16 are side, end and top views, respectively, of the tip of FIGS. 12-13, including hidden lines illustrating internal surface geometry. Naturally, any of the features described in connection with any other embodiment set forth herein can advantageously be applied to this embodiment.

FIG. 17-21 illustrate another embodiment of a penetrating tip 1700 constructed in accordance with the invention having multiple facets 1721, 1723, 1725 on each side thereof, including ovoid facets 1721, and terminating in an arcuate cutting or dissecting surface 1740, similar to the embodiment of FIGS. 7-11. The penetrating tip 1700 includes a body 1710, at its proximal end having a reduced-diameter portion 219, and one or more rotation locking elements 217, as with the foregoing embodiments.

The distal end of the penetrating tip 1700 includes a distal taper 1715 of the body 1710, and opposed angled facets 1721, 1723, 1725, which are angled inwardly, approaching the penetrating edge 1740 at the distal end of the penetrating tip 1700. The facets 1721, 1723, 1725 can be either convex or substantially planar. As illustrated, the facets include a substantially planar facet 1721, and convex facets 1723, 1725, the convexity of which is best seen, for example, in the side view of FIG. 19. The facets 1721, 1723, 1725 are delimited on one side by the contour interface 1730 and at the other side by the cutting or dissecting edge 1740. The change in contours among adjacent facets is defined therebetween at a contour interface indicated by line 1732. The facets 1721 of opposite sides of the penetrating tip 1700 are angled, with respect to one another at an angle α (alpha). The angle α can be anywhere from about 5 degrees to about 80 degrees, at any one degree increment therebetween, for example.

Figure 18:
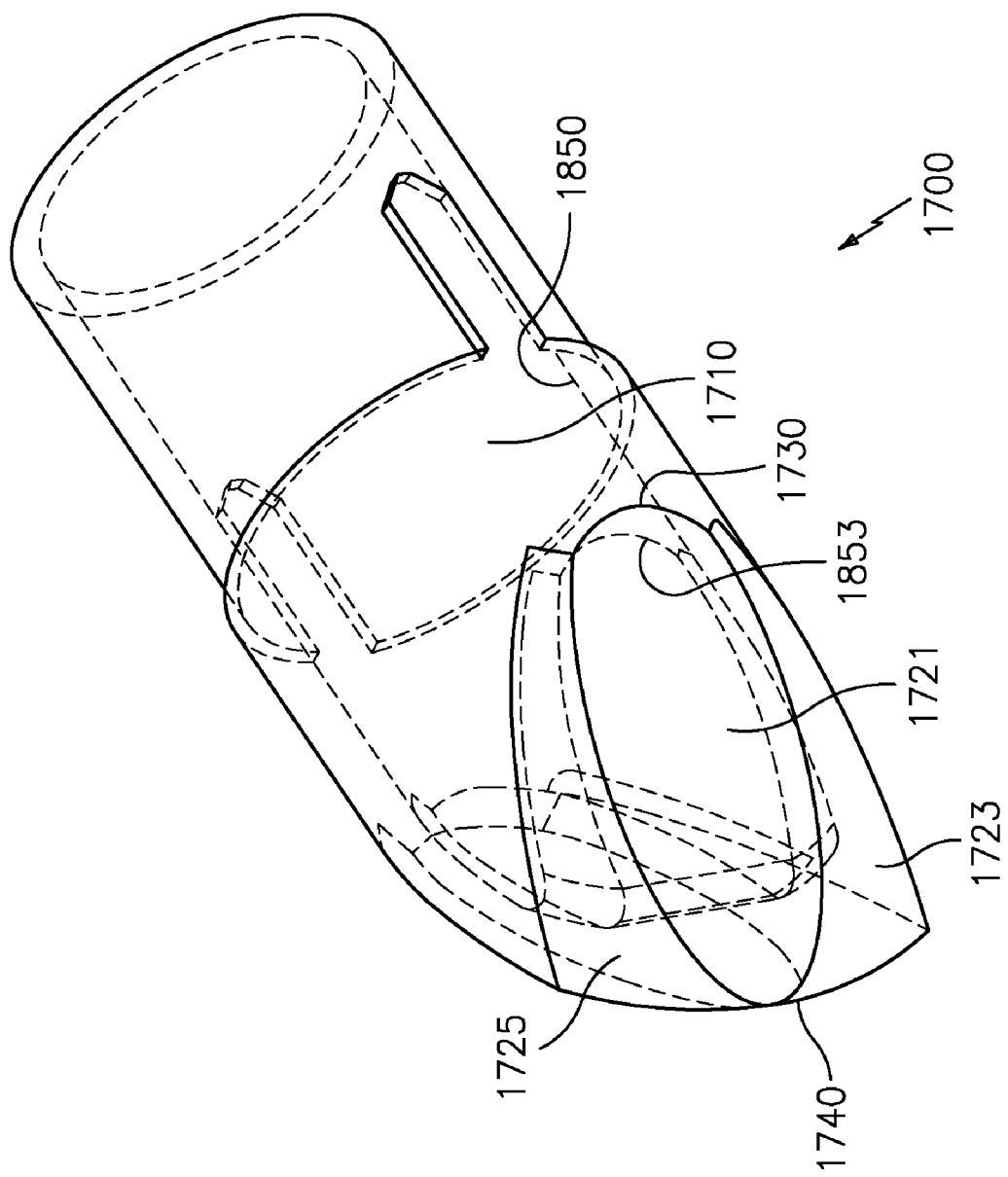
FIG. 18 is an isometric view of the penetrating tip of FIG. 17, including hidden lines illustrating internal surface geometry of the tip.

Naturally, the precise configuration of the facets 1721, 1723, 1725 in this and other embodiments set forth herein can be altered as needed. As can be seen in FIG. 18, the contour interface 1730 includes a corresponding inner contour interface 1853 defined on the inner surface 1850 of the tip 1700, as part of a generally corresponding overall shape.

Figure 17:
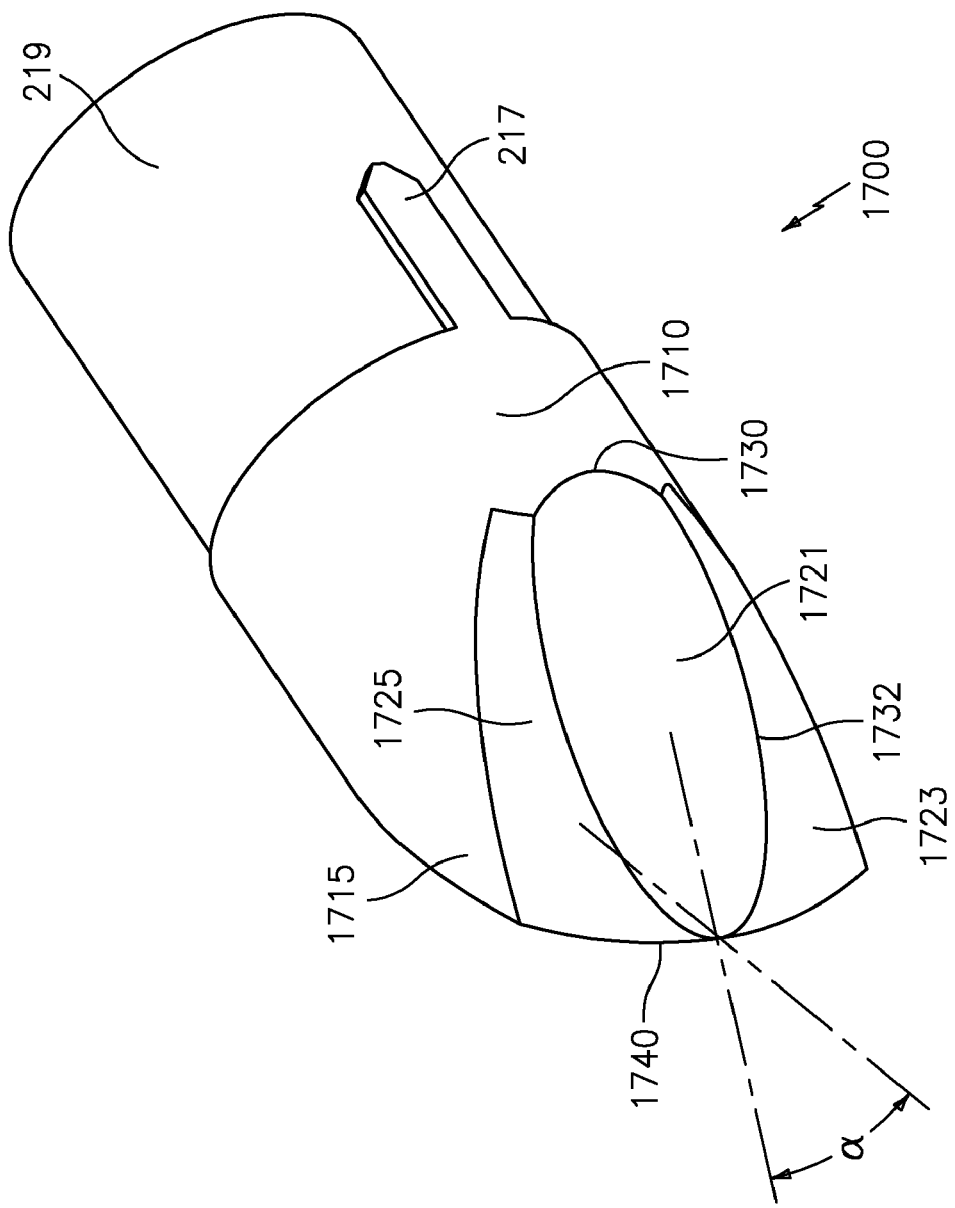
FIG. 17 is another embodiment of a penetrating tip in accordance with the invention having multiple facets on each side thereof, including ovoid facets, and terminating in an arcuate penetrating surface.

FIGS. 19-21 are side, end and top views, respectively of the tip 1700 of FIGS. 17 and 18, including hidden lines illustrating internal surface geometry.

For the purpose of further illustration and not limitation, FIGS. 22A-22F and 23A-D represent further embodiments of a tip 2200 made in accordance with the invention. FIG. 22A depicts a lengthwise view of tip 2200 along one of two opposing substantially ovoid main facets 2220 that converge to a distal dissecting edge 2210. As depicted, facets 2220 are substantially flat, as opposed to concave or convex. Additional smaller facets 2225 are defined between the main facets 2220. As depicted, the intervening facets 2225 are generally elongate concave formations or grooves. It will be appreciated that each of the facets 2220, 2225 may be substantially flat, convex or concave, as desired. FIG. 22B depicts an end view of tip 2200, showing the manner in which all four facets converge and taper to edge 2210. FIG. 22C depicts a lengthwise view of tip 2200 illustrating the shape of facet 2225. FIG. 22D illustrates a cross sectional view of tip 2200 taken along line "A-A" in FIG. 22C. FIG. 22E illustrates a cross sectional view of tip 2200 taken along line "B-B" in FIG. 22A. FIG. 22F illustrates an enlarged cross sectional view of tip 2200 illustrating a locking feature discussed below. FIGS. 23A-C depict similar illustrations of tip 2200 showing the interior surfaces of tip 2200 in broken lines. FIG. 23D depicts an isometric view of tip 2200.

As depicted, tip 2200 defines a hollow interior 2250 bound by a plurality of inner surfaces 2260. A locking feature 2230, if desired, may be provided to facilitate attachment of tip 2200 to a trocar shaft, as described herein. If desired, the tip 2200 may be fully transparent or may include one or more opaque, darkened or otherwise visually obscured regions, such as in the distal region 240 of the tip 2200, proximate the dissecting edge 2210 in region 2240. Such regions are illustrated in the embodiments of FIGS. 24-26 and discussed in further detail below, and can improve visibility of the anatomy being penetrated by reducing glare from stray light entering the tip 2200. As will be appreciated by those of skill in the art, the integral dissecting edge, whether blunt or otherwise, the inwardly tapered opposed planar facets and the opaque distal tip portion of the penetrating tip cooperate to define a continuous outer surface without any openings therethrough. Moreover, as is clearly evident from FIGS. 24-26. the opaque region is preferably adapted to extend around the entire periphery of the tip from a portion proximal to the distal end of the tip to and including the distal end of the tip.

The opaque distal region of the body can minimize glare by reducing errant internal reflections within the tip 2200. Alternatively or additionally, the opaque distal region, which can be colored and in contrast with the remainder of the body of the penetrating tip, can be provided in a manner such that it functions as an indicator or gauge. The term opaque, as used herein, generally refers to an item that substantially inhibits transmission of light. The opaque distal region can be black, gray, blue, white, red, green, purple, pink, yellow, orange or any color desired. Alternatively, if desired, the tip can be translucent and can be clear or have a color imparted thereon. Moreover, the degree of translucidity can be selected as desired, and thus may still act to reduce glare and/or to serve as a gauge or guide. It is also conceived that providing the entire tip or only the distal region 2240 of the tip 2200 with a particular color can serve to act as an optical filter to enhance images obtained therethrough.

As an example, when the colored or obscured distal region 2240 is provided in a trocar used in a surgery, a patient's abdomen can be insufflated normally, and an endoscope inserted through the abdominal wall in a conventional manner. Then, when a trocar having a penetrating tip constructed in accordance with the invention is inserted through the abdominal wall, upon reaching the peritoneum, the distal region (having a color, or other feature), becomes readily visible to the surgeon. This is possible only if the surgeon views the procedure through the endoscope already inserted through the abdominal wall. This, however, may require two separate people to view two separate endoscopes.

By way of further example, FIGS. 24A-24D depict still another embodiment of a tip 2400 made in accordance with the present invention having a plurality of facets 2420, 2425 similar to the embodiment of FIGS. 22-23 and defining a dissecting edge 2410. More particularly, facets 2420 are generally flat surfaces, and facets 2425 are generally concave grooves. It will be appreciated that the shape of facets 2420, 2425 may be modified, as desired to include convex and/or concave surfaces. Locking features 2430 are further provided to facilitate a connection with a trocar tube. Moreover, a distal region 2440 is provided that is generally pyramidal shaped to ease penetration in tissue. As depicted, the distal region 2440 can be darkened, opaque or otherwise obscured, such as by a coating applied thereto, for example, or in another manner.

Such an obscured or opaque region (e.g., 2440) can help reduce the effects of internal reflections in the tip 2400, thus improving viewing. It will be appreciated that all tips disclosed herein may be provided with such an opaque, or otherwise obscured distal region, as desired. The opaque or obscured region may be made by depositing an opaque material on the surface of the tip 2400 in region 2440, such as by screen printing or painting. Moreover, such a region may be provided by treating the surface of the tip to be obscured such as by roughening to substantially prevent light from passing through the region 2440. Alternatively, the obscured region 2440 can be separately formed of an opaque material and combined, by insert molding or other suitable manufacturing technique, with the remaining material of the tip 2400. Alternatively still, the region 2440 may be treated by providing a second material within the material of the tip 2400 in the region 2440 in order to darken the region 2440. The tip 2400 is preferably hollow as with the foregoing embodiments, in order to ease image transmission and to accommodate an endoscope therein for transmitting and receiving light.

FIGS. 25A-25D illustrate still another embodiment of a tip 2500 made in accordance with the invention. As depicted, the tip 2500 includes two facets 2520 similar to the embodiments of FIGS. 22-24. Tip 2500 further includes a generally pyramidal distal region 2540 that is opaque or otherwise obscured. It will be understood that the entirety of tip 2500 may alternatively be transparent, as desired. The distal region 2540 terminates in a tissue separating edge 2510 and locking feature 2530 as with other embodiments described herein. As depicted, tip 2500 further includes two longitudinal depressions 2545 formed therein. Depressions 2545 may facilitate advancement of tip 2500 through tissue by lowering resistance. As depicted, depressions 2545 may be obscured and/or provided with an opaque coating to improve the optical performance of tip 2500. Moreover, the tip 2500 is preferably hollow to accommodate an endoscope, and can be provided with optical features to enhance images obtained therefrom.

By way of still further example, FIGS. 26A-26E illustrate yet another embodiment of a tip 2600 made in accordance with the invention. Tip 2600 includes a plurality of facets 2620 (four identical facets, as depicted) that join each other at edges 2622 and taper to form a distal region 2640 terminating at a penetrating edge 2610. As depicted, distal region 2640 is obscured or opaque, but may be transparent if desired. A locking feature 2630 may further be provided, if desired. As most clearly illustrated in FIG. 26E, the cross section of tip 2600 closely resembles a rectangle with inwardly bowed sides. Such a geometry effectively forms four concave facets 2620 with a reduced cross sectional profile that can facilitate advancement of tip 2600 through tissue by lowering insertion resistance. Tip 2600 is preferably hollow to accommodate an endoscope.

Images can be output from the aforementioned devices—that is in the penetrating tips or in the trocars, for example. The images can be displayed for the surgeon on a monitor arranged in a convenient location. If so-desired, a monitor can be provided at and integrated with the proximal end of the trocar itself, so as to enhance the perception and ergonomic aspects of trocars in accordance with the invention. If so-equipped, the proximal end of the trocar can be configured so as to include one or more integral handles to facilitate gripping of the trocar by the surgeon. Moreover, if so desired, images can be automatically manipulated in real time by a computer, prior to display, so as to reduce or eliminate any distortion, color imbalance or other optical aberrations which may be present in the raw image output from the image sensor.

Penetrating tips and trocars in accordance with the invention can be used to create an opening in an anatomical structure of a patient, such in the patient's abdominal wall. The opening can be used to provide access or any of a variety of instruments, such as, for example, a feeding tube. However, it is particularly envisioned, that devices constructed in accordance with the invention will be used to insert surgical access devices, such as access ports and cannulas, which maintain the opening formed by a trocar and therefore provide easy access to a surgical cavity. Some example access devices are set forth in U.S. patent application Ser. No. 11/517,929, filed Sep. 8, 2006 entitled "Trocar Assembly with Pneumatic Sealing," which application is incorporated herein by reference, in its entirety. Access devices described in the aforementioned application include various types of seals to inhibit escape of insufflation gas from a patient's peritoneal cavity during a surgical procedure. Additionally, devices constructed in accordance with the invention can be used to insert flexible access devices, such as those set forth in the application entitled "Elastically Deformable Surgical Access Device" U.S. patent application Ser. No. 11/544,856, filed Oct. 6, 2006, which application is also incorporated herein by reference in its entirety. If used with such elastically deformable surgical access devices, engagement elements can be provided on the trocar or the penetrating tip to enable engagement with such access device.

Following preparation of the patient, a trocar having a tip in accordance with the invention is used to pierce the abdominal wall of the patient. The surgeon is able to view the tissue being penetrated by the penetrating tip through any of the aforementioned means, such as through a video monitor. Typically, a surgical access device, as those described above, will be inserted simultaneously through the opening created by the trocar. Thus, prior to insertion, the trocar with the penetrating tip is inserted through the access device such that the penetrating tip protrudes from the end of the access port, and the penetrating tip, surrounded by the access port, is inserted through the abdominal wall. In one technique, a scalpel is used to make an incision through the skin, and the penetrating tip with the trocar and access port is inserted through the remaining layers of tissue into the abdominal wall. The trocar is then removed, leaving the surgical access device in place in order to carry out the prescribed surgical procedure.

Further, the present invention encompasses methods of use of the devices described herein. For example, the present invention includes methods of use of penetrating tips described herein, in combination with insertion devices, such as trocars or obturators, and surgical access devices, such as cannulas.

Further it is envisioned that the present invention can relate to a kit having one or more of a penetrating tip in accordance with the invention, a surgical access device, such as a cannula, and an insertion device, such as a trocar or obturator.

It will be apparent to those skilled in the art that various modifications and variations can be made to devices of the present invention without departing from the spirit or scope of the invention.

What is claimed is:

1. A penetrating tip for a surgical trocar, the penetrating tip comprising:
   (a) a generally transparent body having opposed proximal and distal ends, the body including an opaque distal tip portion having a generally pyramidal shape configured to ease penetration through tissue, wherein the opacity of the distal tip portion helps to reduce internal reflections within the tip;

(b) an integral dissecting edge arranged at the distal end of the body;

(c) a pair of inwardly tapered opposed planar facets formed in the body, converging with one another at the integral dissecting edge; and (d) a pair of opposed curved facets formed in the body, separating the pair of inwardly tapered opposed planar facets from one another and extending distally toward the integral dissecting edge.

2. The penetrating tip of claim 1, the tip further comprising an expanded-diameter region for engaging a surgical access device.

3. The penetrating tip of claim 1, wherein the opposed curved facets are concave grooves.

4. The penetrating tip of claim 1, wherein the opposed inwardly tapered planar facets are provided on the tip at about a 20 degree angle with respect to one another.

5. The penetrating tip of claim 1, wherein the opposed inwardly tapered planar facets are provided on the tip at about a 30 degree angle with respect to one another.

6. The penetrating tip of claim 1, wherein the integral dissecting edge is substantially straight in configuration.

7. The penetrating tip of claim 1, wherein a locking element is provided on the body for engaging an obturator.

8. The penetrating tip of claim 1, wherein the tip further includes an inner optical surface configured so as to minimize distortion of images taken through the penetrating tip.

9. The penetrating tip of claim 1, wherein the tip consists of a plastic material.

10. The penetrating tip of claim 1, wherein the tip is formed of polycarbonate plastic.

11. The penetrating tip of claim 1, wherein the tip is formed of polymethyl methacrylate.

12. A surgical trocar comprising:

(a) a handle;

(b) an elongated shaft extending distally from the handle; and (c) a penetrating tip operatively associated with a distal end portion of the elongated shaft, the penetrating tip including:

(i) a generally transparent body having proximal and distal ends, the body having an opaque distal tip portion having a generally pyramidal shape configured to ease penetration through tissue, wherein the opacity of the distal tip portion helps to reduce internal reflections within the tip;

(ii) an integral dissecting edge arranged at the distal end of the body;

(iii) a pair of inwardly tapered opposed planar facets formed in the body, converging with one another at the integral dissecting edge; and (iv) a pair of opposed curved facets formed in the body, separating the pair of inwardly tapered opposed planar facets from one another and extending distally toward the integral dissecting edge.

13. The surgical trocar of claim 12, further comprising an optical path extending from the tip to an imaging device.

14. The surgical trocar of claim 13, wherein the imaging device is a CCD sensor.

15. The surgical trocar of claim 13, wherein the imaging device is an optical eyepiece.

16. The surgical trocar of claim 13, wherein the imaging device is provided in the shaft of the surgical trocar.

17. The surgical trocar of claim 13, wherein the imaging device is provided external to the surgical trocar.

18. The surgical trocar of claim 12, further comprising an access device configured and dimensioned to receive the shaft of the trocar such that the penetrating tip protrudes from the end of the access device.

19. The penetrating tip of claim 1, wherein the opaque distal tip portion has an opaque coating applied thereto.

20. The penetrating tip of claim 19, wherein the opaque coating includes paint.

21. The penetrating tip of claim 19, wherein the opaque coating is screen printed onto the distal tip portion.

22. The penetrating tip of claim 1, wherein the tip defines an enclosed interior therein disposed between the inwardly tapered opposed planar facets.

23. The surgical trocar of claim 12, wherein the integral dissecting edge is blunt such that the tip is adapted and configured to prevent accidental injury to internal anatomical structures.

24. The penetrating tip of claim 1, wherein the integral dissecting edge is blunt.

* * * * *